United States Patent [19]

Morton, Jr.

[11] 4,082,782
[45] Apr. 4, 1978

[54] 13,14-DIHYDRO-PGD₁, ANALOGS

[75] Inventor: Douglas Ross Morton, Jr., Portage, Mich.

[73] Assignee: The Upjohn Company, Kalamazoo, Mich.

[21] Appl. No.: 756,098

[22] Filed: Dec. 30, 1976

Related U.S. Application Data

[62] Division of Ser. No. 614,242, Sep. 17, 1975, Pat. No. 4,016,184.

[51] Int. Cl.² .......................................... C07C 177/00
[52] U.S. Cl. ............................ 260/408; 260/410.9 R; 260/413; 260/514 D; 560/121
[58] Field of Search .......... 260/468 D, 514 D, 514 C, 260/514 A

[56] References Cited

U.S. PATENT DOCUMENTS 3,878,239  4/1975  Hayashi et al. ..................... 260/514

Primary Examiner—Robert Gerstl
Attorney, Agent, or Firm—Robert A. Armitage

[57] ABSTRACT

Prostaglandin analogs with the following cyclopentane ring structure:

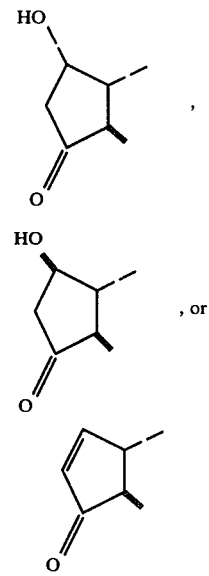

are disclosed along with intermediates useful in their preparation and processes for their preparation. These analogs are useful for the same pharmacological purposes as the prostaglandins, particularly and especially as blood platelet aggregation inhibitors.

49 Claims, No Drawings

13,14-DIHYDRO-PGD$_1$, ANALOGS

The present application is a divisional application of Ser. No. 614,242, filed Sep. 17, 1975, now issued as U.S. Pat. No. 4,016,184, on Apr. 5, 1977.

The present invention relates to prostaglandin analogs for which the essential material constituting a disclosure therefor is incorporated by reference here from U.S. Pat. No. 4,016,184, issued Apr. 5, 1977.

I claim:

1. A prostaglandin analog of the formula

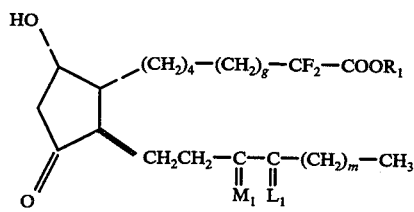

wherein $g$ is one, 2, or 3;
wherein $M_1$ is

or

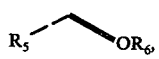

wherein $R_5$ and $R_6$ are hydrogen or methyl, with the proviso that one of $R_5$ and $R_6$ is methyl only when the other is hydrogen;
wherein $L_1$ is

or a mixture of

wherein $R_3$ and $R_4$ are hydrogen, methyl, or fluoro, being the same or different, with the proviso that one of $R_3$ and $R_4$ is fluoro only when the other is hydrogen or fluoro;
wherein $m$ is one to 5, inclusive; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein $g$ is one.

3. A compound according to claim 2, wherein $m$ is 3.

4. A compound according to claim 3, wherein at least one of $R_3$ and $R_4$ is fluoro.

5. A compound according to claim 4, wherein $R_3$ and $R_4$ are both fluoro.

6. A compound according to claim 5, wherein $R_5$ and $R_6$ are hydrogen.

7. 2,2,16,16-Tetrafluoro-13,14-dihydro-PGD$_1$, a compound according to claim 6.

8. A compound according to claim 3, wherein at least one of $R_3$ and $R_4$ is methyl.

9. A compound according to claim 8, wherein $R_3$ and $R_4$ are both methyl.

10. A compound according to claim 9, wherein $R_5$ and $R_6$ are both hydrogen.

11. 2,2-Difluoro-16,16-dimethyl-13,14-dihydro-PGD$_1$, a compound according to claim 10.

12. A compound according to claim 3, wherein $R_3$ and $R_4$ are both hydrogen.

13. A compound according to claim 12, wherein $R_5$ and $R_6$ are both hydrogen.

14. 2,2-Difluoro-13,14-dihydro-PGD$_1$, a compound according to claim 13.

15. A compound according to claim 12, wherein $R_5$ is methyl.

16. 2,2-Difluoro-15-methyl-13,14-dihydro-PGD$_1$, a compound according to claim 15.

17. A compound according to claim 12, wherein $R_6$ is methyl.

18. 2,2-Difluoro-13,14-dihydro-PGD$_1$, 15-methyl ether, a compound according to claim 17.

19. A prostaglandin analog of the formula

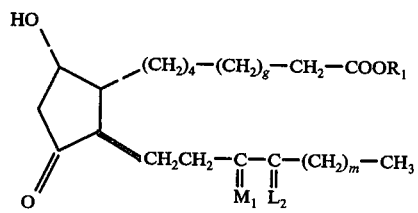

wherein $g$ is one, 2, or 3;
wherein $M_1$ is

or

wherein $R_5$ and $R_6$ are hydrogen or methyl, with the proviso that one of $R_5$ and $R_6$ is methyl only when the other is hydrogen;
wherein $L_2$ is

or a mixture of

and

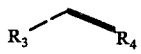

wherein R₃ and R₄ are hydrogen or fluoro, being the same or different, with the proviso that at least one of R₃ and R₄ is fluoro;

wherein m is one to 5, inclusive; and wherein R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substitutes with one, two, or three chloro or alkyl of one to 3 carbon atoms, inclusive, or a pharmacologically acceptable cation.

20. A compound according to claim 19, wherein g is 3.

21. A compound according to claim 20, wherein m is 3.

22. A compound according to claim 21, wherein R₃ and R₄ are both fluoro.

23. A compound according to claim 22, wherein R₅ and R₆ are hydrogen.

24. 2a,2b-Dihomo-16,16-difluoro-13,14-dihydro-PGD₁, a compound according to claim 23.

25. A compound according to claim 19, wherein g is one.

26. A compound according to claim 25, wherein m is 3.

27. A compound according to claim 26, wherein both R₃ and R₄ are fluoro.

28. A compound according to claim 27, wherein R₅ and R₆ are hydrogen.

29. 16,16-Difluoro-13,14-dihydro-PGD₁, a compound according to claim 28.

30. A prostaglandin analog of the formula

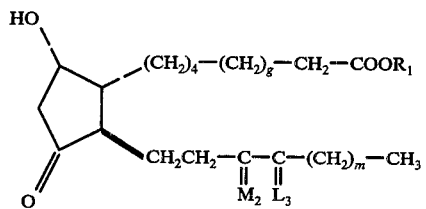

wherein g is one, 2, or 3;
wherein M₂ is

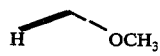

or

wherein L₃ is

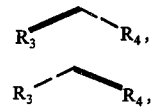

or a mixture of

and

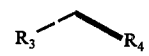

wherein R₃ and R₄ are hydrogen or methyl, being the same or different;

wherein m is one to 5, inclusive; and wherein R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

31. A compound according to claim 30, wherein g is one.

32. A compound according to claim 31, wherein m is 3.

33. A compound according to claim 32, wherein at least one of R₃ and R₄ is methyl.

34. A compound according to claim 33, wherein R₃ and R₄ are both methyl.

35. A compound according to claim 32, wherein R₃ and R₄ are hydrogen.

36. 13,14-Dihydro-PGD₁, 15-methyl ether, a compound according to claim 35.

37. A prostaglandin analog of the formula

[structure with (CH₂)₄—(CH₂)₉—CH₂—COOR₁ and CH₂CH₂—C—C—(CH₂)ₘ—CH₃ with M₃ L₄]

wherein g is one, 2, or 3;
wherein M₃ is

or

wherein R₅ is hydrogen or methyl; wherein L₄ is

[R₃ R₄ structure],

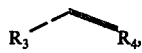

or a mixture of

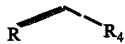

and

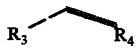

wherein R₃ and R₄ are hydrogen or methyl, being the same or different, with the proviso that one of R₃ and R₄ is methyl;

wherein $m$ is one to 5, inclusive; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

38. A compound according to claim 37, wherein $g$ is 3.

39. A compound according to claim 38, wherein $m$ is 3.

40. A compound according to claim 39, wherein R₃ and R₄ are both methyl.

41. A compound according to claim 40, wherein R₅ is hydrogen.

42. 2a,2b-Dihomo-16,16-dimethyl-13,14-dihydro-PGD₁, a compound according to claim 41.

43. A compound according to claim 37, wherein $g$ is one.

44. A compound according to claim 43, wherein $m$ is 3.

45. A compound according to claim 44, wherein R₃ and R₄ are both methyl.

46. A compound according to claim 45, wherein R₅ is hydrogen.

47. 16,16-Dimethyl-13,14-dihydro-PGD₁, a compound according to claim 46.

48. A prostaglandin analog of the formula

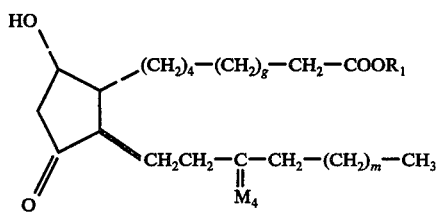

wherein $g$ is one, 2, or 3;
wherein M₄ is

or

wherein $m$ is one to 5; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation.

49. 15-methyl-13,14-dihydro-PGD₁, a compound according to claim 48.

* * * * *

UNITED STATES PATENT OFFICE
CERTIFICATE OF CORRECTION

Patent No. 4,082,782            Dated       April 4, 1978

Inventor(s) Douglas R. Morton, Jr.

It is certified that error appears in the above-identified patent and that said Letters Patent are hereby corrected as shown below:

Column 3, lines 1-3, should read -- 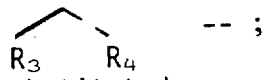 -- ;

line 19, "substitutes" should read -- substituted --;

Column 4, lines 11-13, should read -- 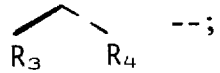 --;

Column 5, lines 7-9, should read -- 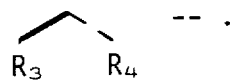 -- .

Signed and Sealed this

*Third* Day of *October 1978*

[SEAL]

Attest:

RUTH C. MASON
*Attesting Officer*

DONALD W. BANNER
*Commissioner of Patents and Trademarks*